United States Patent
Eng et al.

(10) Patent No.: US 12,105,099 B2
(45) Date of Patent: Oct. 1, 2024

(54) METHODS AND DEVICES FOR QUANTITATIVELY ESTIMATING SYNDECAN-1

(71) Applicants: Richard Eng, Baltimore, MD (US); Cassandra Parent, Baltimore, MD (US); Amal Hayat, Baltimore, MD (US); Amanda Ruci, Baltimore, MD (US); Anvith Krishnan, Baltimore, MD (US); Feiyang Huang, Baltimore, MD (US); Eric Simon, Baltimore, MD (US); Ellie Zhang, Baltimore, MD (US)

(72) Inventors: Richard Eng, Baltimore, MD (US); Cassandra Parent, Baltimore, MD (US); Amal Hayat, Baltimore, MD (US); Amanda Ruci, Baltimore, MD (US); Anvith Krishnan, Baltimore, MD (US); Feiyang Huang, Baltimore, MD (US); Eric Simon, Baltimore, MD (US); Ellie Zhang, Baltimore, MD (US)

(73) Assignee: DIOTEX DIAGNOSTICS, LLC, Oakland, MD (US)

( * ) Notice: Subject to any disclaimer, the term of this patent is extended or adjusted under 35 U.S.C. 154(b) by 388 days.

(21) Appl. No.: 17/715,294

(22) Filed: Apr. 7, 2022

(65) Prior Publication Data

US 2022/0349905 A1  Nov. 3, 2022

Related U.S. Application Data

(60) Provisional application No. 63/180,762, filed on Apr. 28, 2021.

(51) Int. Cl.
| | | |
|---|---|---|
| G01N 33/53 | (2006.01) | |
| G01N 33/543 | (2006.01) | |
| G01N 33/553 | (2006.01) | |
| G01N 33/68 | (2006.01) | |
| B82Y 5/00 | (2011.01) | |
| B82Y 40/00 | (2011.01) | |

(52) U.S. Cl.
CPC ... *G01N 33/6893* (2013.01); *G01N 33/54346* (2013.01); *G01N 33/54388* (2021.08); *G01N 33/553* (2013.01); *B82Y 5/00* (2013.01); *B82Y 40/00* (2013.01)

(58) Field of Classification Search
CPC ........ G01N 33/6893; G01N 33/54388; G01N 33/54346; G01N 33/553; G01N 33/543
See application file for complete search history.

(56) References Cited

U.S. PATENT DOCUMENTS

| | | | | |
|---|---|---|---|---|
| 8,221,995 B2 * | 7/2012 | Lee | ................ | G01N 33/6893 435/7.94 |
| 9,851,364 B2 * | 12/2017 | Ellis | ................ | G01N 33/558 |
| 2004/0248322 A1 * | 12/2004 | Charlton | ............ | G01N 33/558 436/518 |
| 2011/0300122 A1 * | 12/2011 | Fries | ............ | A61P 7/04 424/94.64 |
| 2012/0135427 A1 * | 5/2012 | Kypros | ................ | G01N 33/74 435/7.92 |
| 2012/0315266 A1 | 12/2012 | Olson et al. | | |
| 2013/0072580 A1 * | 3/2013 | Barasch | ............ | G01N 33/6893 435/7.1 |
| 2013/0273528 A1 * | 10/2013 | Ehrenkranz | ........... | G01N 33/558 435/7.9 |
| 2014/0242613 A1 * | 8/2014 | Takeuchi | ............ | G01N 33/558 435/7.32 |
| 2019/0079085 A1 | 3/2019 | Lawrence et al. | | |

FOREIGN PATENT DOCUMENTS

WO  2021/062298 A1  4/2021

OTHER PUBLICATIONS

Mosaad et al., Study of serum syndecan-1 levels in a group of Egyptian juvenile systemic lupus erythematosus patients, Immunology Letters 181, 2017, pp. 16-19. (Year: 2017).*

Haywood-Watson et al., Modulation of syndecan-1 shedding after hemorrhagic shock and resuscitation, PLoS ONE, Aug. 2011, vol. 6, Issue 8, pp. 1-10. (Year: 2011).*

An English translation of the International Search Report and Written Opinion dated Jul. 13, 2022, from corresponding PCT International Application No. PCT/US2022/024967.

International Preliminary Report on Patentability issued Oct. 24, 2023 in counterpart PCT/US2022/024967, ten (10) pages.

* cited by examiner

*Primary Examiner* — Gary Counts
(74) *Attorney, Agent, or Firm* — DLA PIPER LLP (US)

(57) ABSTRACT

This disclosure provides methods and devices for determining a quantitative estimate of syndecan-1 levels in a mammalian subject suspected of internal hemorrhaging. The method includes applying a blood sample from the subject to a hand-held assay device capable of providing optical quantitation of the amount of syndecan-1 in the sample, measuring, by means of said assay device, an analyte signal value correlated to a concentration of the syndecan-1 in the blood sample and comparing the analyte signal value to a minimum threshold, wherein an analyte signal value less than the minimum threshold indicates that the subject is not internally hemorrhaging, and an analyte signal value above the minimum threshold indicates the subject is internally hemorrhaging. The methods and devices are adapted to rapidly assess internal hemorrhaging and hemorrhagic shock in a patient outside of hospital settings.

10 Claims, 1 Drawing Sheet

Specification includes a Sequence Listing.

SEQUENCE LISTING

```
<160> NUMBER OF SEQ ID NOS: 5

<210> SEQ ID NO 1
<211> LENGTH: 288
<212> TYPE: PRT
<213> ORGANISM: Homo sapiens

<400> SEQUENCE: 1

Gln Ile Val Ala Thr Asn Leu Pro Pro Glu Asp Gln Asp Gly Ser Gly
1               5                   10                  15

Asp Asp Ser Asp Asn Phe Ser Gly Ser Gly Ala Gly Ala Leu Gln Asp
            20                  25                  30

Ile Thr Leu Ser Gln Gln Thr Pro Ser Thr Trp Lys Asp Thr Gln Leu
```

|   |   | 35 |   |   |   | 40 |   |   |   | 45 |   |
|---|---|---|---|---|---|---|---|---|---|---|---|

Leu Thr Ala Ile Pro Thr Ser Pro Glu Pro Thr Gly Leu Glu Ala Thr
  50                     55                   60

Ala Ala Ser Thr Ser Thr Leu Pro Ala Gly Glu Gly Pro Lys Glu Gly
65                    70                   75                 80

Glu Ala Val Val Leu Pro Glu Val Glu Pro Gly Leu Thr Ala Arg Glu
                 85                   90                 95

Gln Glu Ala Thr Pro Arg Pro Arg Glu Thr Thr Gln Leu Pro Thr Thr
            100                 105              110

His Leu Ala Ser Thr Thr Thr Ala Thr Thr Ala Gln Glu Pro Ala Thr
        115                   120              125

Ser His Pro His Arg Asp Met Gln Pro Gly His His Glu Thr Ser Thr
    130                 135                140

Pro Ala Gly Pro Ser Gln Ala Asp Leu His Thr Pro His Thr Glu Asp
145                  150                155           160

Gly Gly Pro Ser Ala Thr Glu Arg Ala Ala Glu Asp Gly Ala Ser Ser
            165                 170              175

Gln Leu Pro Ala Ala Glu Gly Ser Gly Glu Gln Asp Phe Thr Phe Glu
            180                 185              190

Thr Ser Gly Glu Asn Thr Ala Val Val Ala Val Glu Pro Asp Arg Arg
        195                   200              205

Asn Gln Ser Pro Val Asp Gln Gly Ala Thr Gly Ala Ser Gln Gly Leu
    210                 215                220

Leu Asp Arg Lys Glu Val Leu Gly Gly Val Ile Ala Gly Gly Leu Val
225                  230                235           240

Gly Leu Ile Phe Ala Val Cys Leu Val Gly Phe Met Leu Tyr Arg Met
            245                 250              255

Lys Lys Lys Asp Glu Gly Ser Tyr Ser Leu Glu Glu Pro Lys Gln Ala
            260                 265              270

Asn Gly Gly Ala Tyr Gln Lys Pro Thr Lys Gln Glu Glu Phe Tyr Ala
        275                   280              285

<210> SEQ ID NO 2
<211> LENGTH: 232
<212> TYPE: PRT
<213> ORGANISM: Homo sapiens

<400> SEQUENCE: 2

Gln Ile Val Ala Thr Asn Leu Pro Pro Glu Asp Gln Asp Gly Ser Gly
1                  5                   10                 15

Asp Asp Ser Asp Asn Phe Ser Gly Ser Gly Ala Gly Ala Leu Gln Asp
            20                 25              30

Ile Thr Leu Ser Gln Gln Thr Pro Ser Thr Trp Lys Asp Thr Gln Leu
      35                  40                45

Leu Thr Ala Ile Pro Thr Ser Pro Glu Pro Thr Gly Leu Glu Ala Thr
  50                    55                   60

Ala Ala Ser Thr Ser Thr Leu Pro Ala Gly Glu Gly Pro Lys Glu Gly
65                  70                   75                 80

Glu Ala Val Val Leu Pro Glu Val Glu Pro Gly Leu Thr Ala Arg Glu
                 85                   90                 95

Gln Glu Ala Thr Pro Arg Pro Arg Glu Thr Thr Gln Leu Pro Thr Thr
            100                 105              110

His Leu Ala Ser Thr Thr Thr Ala Thr Thr Ala Gln Glu Pro Ala Thr
        115                   120              125

```
Ser His Pro His Arg Asp Met Gln Pro Gly His His Glu Thr Ser Thr
    130                 135                 140

Pro Ala Gly Pro Ser Gln Ala Asp Leu His Thr Pro His Thr Glu Asp
145                 150                 155                 160

Gly Gly Pro Ser Ala Thr Glu Arg Ala Ala Asp Gly Ala Ser Ser
                165                 170                 175

Gln Leu Pro Ala Ala Glu Gly Ser Gly Glu Gln Asp Phe Thr Phe Glu
            180                 185                 190

Thr Ser Gly Glu Asn Thr Ala Val Val Ala Val Glu Pro Asp Arg Arg
            195                 200                 205

Asn Gln Ser Pro Val Asp Gln Gly Ala Thr Gly Ala Ser Gln Gly Leu
    210                 215                 220

Leu Asp Arg Lys Glu Val Leu Gly
225                 230

<210> SEQ ID NO 3
<211> LENGTH: 21
<212> TYPE: PRT
<213> ORGANISM: Homo sapiens

<400> SEQUENCE: 3

Gly Val Ile Ala Gly Gly Leu Val Gly Leu Ile Phe Ala Val Cys Leu
1               5                   10                  15

Val Gly Phe Met Leu
            20

<210> SEQ ID NO 4
<211> LENGTH: 35
<212> TYPE: PRT
<213> ORGANISM: Homo sapiens

<400> SEQUENCE: 4

Tyr Arg Met Lys Lys Lys Asp Glu Gly Ser Tyr Ser Leu Glu Glu Pro
1               5                   10                  15

Lys Gln Ala Asn Gly Gly Ala Tyr Gln Lys Pro Thr Lys Gln Glu Glu
            20                  25                  30

Phe Tyr Ala
        35

<210> SEQ ID NO 5
<211> LENGTH: 99
<212> TYPE: PRT
<213> ORGANISM: Homo sapiens

<400> SEQUENCE: 5

Thr Thr Thr Ala Thr Thr Ala Gln Glu Pro Ala Thr Ser His Pro His
1               5                   10                  15

Arg Asp Met Gln Pro Gly His His Glu Thr Ser Thr Pro Ala Gly Pro
            20                  25                  30

Ser Gln Ala Asp Leu His Thr Pro His Thr Glu Asp Gly Gly Pro Ser
        35                  40                  45
```

-continued

```
Ala Thr Glu Arg Ala Ala Glu Asp Gly Ala Ser Ser Gln Leu Pro Ala
    50                  55                  60
Ala Glu Gly Ser Gly Gln Asp Phe Thr Phe Glu Thr Ser Gly Glu
65              70                  75                  80
Asn Thr Ala Val Val Ala Val Glu Pro Asp Arg Arg Asn Gln Ser Pro
                85                  90                  95
Val Asp Gln
```

METHODS AND DEVICES FOR QUANTITATIVELY ESTIMATING SYNDECAN-1

SEQUENCE LISTING

The instant application contains a Sequence Listing which has been submitted electronically in ASCII format and is hereby incorporated by reference in its entirety. Said ASCII copy, created on Apr. 4, 2022, is named BED-21-1111R_(000125-017141)_SL.txt and is 6,381 bytes in size.

TECHNICAL FIELD

This disclosure relates to methods and devices for quantitatively estimating syndecan-1 levels in a mammalian subject. Advantageously, the methods and devices are adapted to rapidly assess internal hemorrhaging and hemorrhagic shock in a patient outside of hospital settings.

BACKGROUND

Hemorrhagic shock, a condition where the body shuts off critical functions such as breathing and consciousness, is triggered by heavy internal or external bleeding. Early diagnosis is critical for administering emergency treatment in the field or rapid evacuation to a surgical facility that can administer proper treatment. Tran, Alexandre, et al. "Early Identification of Patients Requiring Massive Transfusion, Embolization, or Hemostatic Surgery for Traumatic Hemorrhage: a Systematic Review Protocol." *Systematic Reviews*, vol. 6(1) 2017. While external bleeding is easy to diagnose, internal bleeding generally requires a physician's suspicion and subsequent examination. Johnson, A. & Burns, B. "Hemorrhage." *StatPearls*. 2020.

Within hospital settings, these examinations can be confirmed via imaging and the patient can easily receive the necessary prompt surgical care. Ahmed N, Kassavin D, Kuo Y, et al. "Sensitivity and Specificity of CT Scan and Angiogram for Ongoing Internal Bleeding Following Torso Trauma." *Emergency Medicine Journal*, vol. 30, 2013. However, outside of hospital settings, such as in combat situations or at sites where traumatic injuries have occurred, imaging is impractical, and the early signs of hemorrhage are often masked by the body's stress response as a consequence of battle or a traumatic event. Johnson, Michael, et. al. "Compensatory Reserve Index: Performance of A Novel Monitoring Technology to Identify the Bleeding Trauma Patient." *Shock: Injury Inflammation, and Sepsis laboratory and Clinical Approaches*, vol. 49(3), pgs. 295-300. Thus, current methods for hemorrhage detection are inadequate as they require specialized equipment and highly trained personnel.

As hemorrhaging causes an estimated 90% of preventable U.S. troop deaths and over 50,000 U.S. civilian deaths, there is a need for a fast, accessible, and accurate hemorrhagic diagnostic tool designed to minimize this loss of life. Spinella, Philip. "Zero preventable deaths after traumatic injury: An achievable goal." Trauma Acute Care Surgery, vol. 82(6), 2017; Cannon, Jeremy. "Hemorrhagic Shock." New England Journal of Medicine, vol. 378(4), 2015.

SUMMARY

We provide methods and devices for determining a quantitative estimate of syndecan-1 levels in a mammalian subject suspected of internal hemorrhaging. The method includes applying a blood sample from the subject to a hand-held assay device capable of providing optical quantitation of the amount of syndecan-1 in the sample, measuring, by means of said assay device, an analyte signal value correlated to a concentration of the syndecan-1 in the blood sample and comparing the analyte signal value to a minimum threshold, wherein an analyte signal value less than the minimum threshold indicates that the subject is not internally hemorrhaging, and an analyte signal value above the minimum threshold indicates the subject is internally hemorrhaging. The methods and devices are adapted to rapidly assess internal hemorrhaging and hemorrhagic shock in a patient outside of hospital settings.

DETAILED DESCRIPTION

Figure 1:
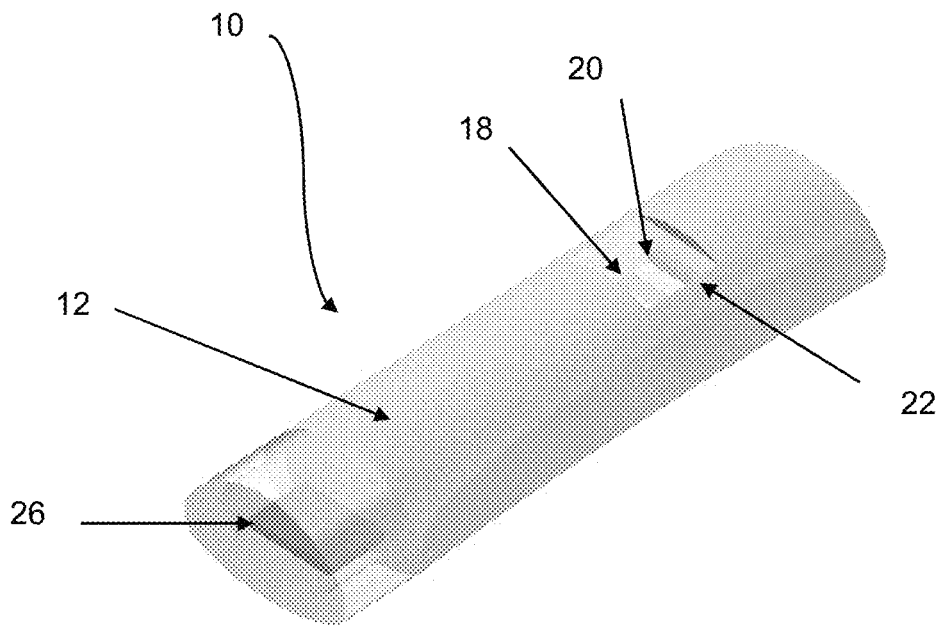
FIG. 1 shows an exemplary device of this disclosure.

This disclosure provides methods and devices for quantitatively estimating syndecan-1 levels in a mammalian subject to assess internal hemorrhaging and hemorrhagic shock. The methods and devices of this disclosure advantageously improve existing technology by providing a form factor that is both highly portable and fast-acting. The devices can be easily carried by field medics or EMTs and used in the field to rapidly confirm if a patient is likely to be suffering from internal hemorrhaging and hemorrhagic shock. The ability to obtain confirmation of internal hemorrhaging and hemorrhagic shock in the field, especially in the early stages, means that a patient can be identified for treatment on site and evacuated to a hospital during a critical window after onset of injury. This is especially useful in triage situations where many people may have been injured and field medics must identify those most critically injured and in need of immediate care. Early determination and treatment of internal hemorrhaging and hemorrhagic can vastly improve patient outcomes.

Aspects of this disclosure utilize chemical mechanism of a syndecan-1 anti syndecan-1 antibody reaction. Syndecan-1 is a proteoglycan that promotes interaction with plasma proteins. Syndecan-1 is transmembrane protein encoded by the SDC1 gene (also referred to as SYND1 and CD138). See, e.g., UniProtKB—P18827. The amino acid sequence of syndecan-1 is provided in SEQ ID NO:1. The extracellular domain of syndecan-1 (CD138) is provided in SEQ ID NO: 2. The transmembrane domain is provided in SEQ ID NO: 3. The cytosolic domain is provided in SEQ ID NO: 4.

While syndecan-1 is found primarily on epithelial cells, it also found on endothelial cells and plays an important role in endothelial cell function after hemorrhagic shock. Immediately after blood vessel injury, the lining of the damaged vessels begins to shed glycocalyx from endothelial cells, and syndecan-1 is a component of this glycocalyx. Patients who undergo traumatic injury experience elevated levels of syndecan-1 after injury. While normal, healthy adults have approximately 27±1 ng/ml of syndecan-1 in their blood, patients experiencing hemorrhage have an average of 554±93 ng/ml of syndecan-1. Haywood-Watson R J, Holcomb J B, Gonzalez E A, Peng Z, Pati S, et al. (2011) Modulation of Syndecan-8 Shedding after Hemorrhagic Shock and Resuscitation. *PLoS ONE* 6(8): e23530. In addition, porcine models demonstrated that this increase in concentration occurs early in the earliest stage of hemorrhage, meaning that there is still time for effective treatment to occur. Sillesen M., Rasmussen L. S., Jin G., Jepsen C. H., Imam A, et. al. "Assessment of coagulopathy, endothelial injury, and inflammation after traumatic brain injury and hemorrhage in a porcine model." *J Trauma Acute Care Surg*, 76(1):12-9, 2014. As an early-stage biomarker of internal hemorrhaging and hemorrhagic shock, syndecan-1 has been identified by the inventors as a useful analyte in a biology-based test to assess and diagnose internal bleeding.

Aspects of this disclosure relate to methods and devices taking advantage of the biochemical and optical principles of a "one-pot" assay and applying them in an accessible form factor. For example, preferred devices and methods may employ a lateral flow assay (LFA) in order to simplify sample preparation and advantageously may provide a colorimetric test result that can be observed without laboratory equipment. Preferred examples utilize blood microsampling, such as the finger prick method, in order to collect a test specimen. This specimen will then be transferred to the collection site on the device. This is as simple as the user input would need to be. Within 5 to 15 minutes, the presence of a color shifted line on the device will indicate an elevated level of syndecan-1 correlated with internal hemorrhaging. The absence of such a line will indicate a lack of internal hemorrhaging in the patient.

Figure 2:
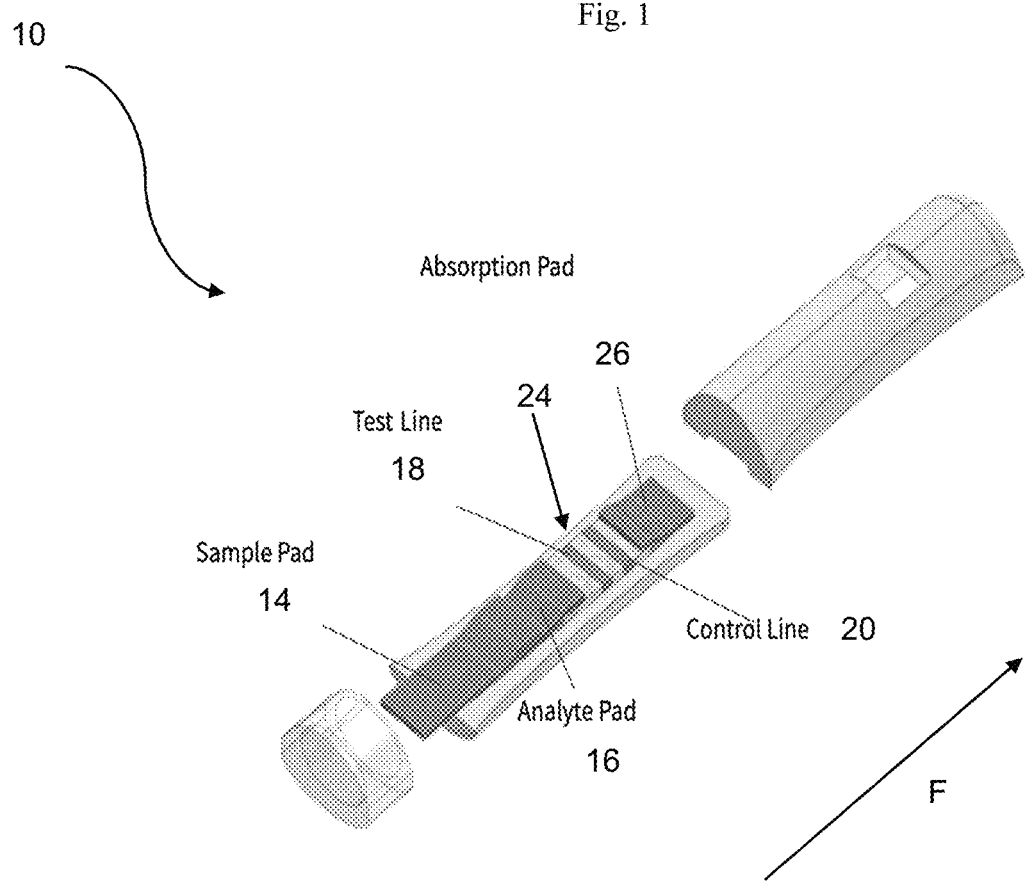
FIG. 2 shows an exploded view of an exemplary device of this disclosure.

FIGS. 1 and 2 depict an exemplary assay device 10 for quantitative estimation of syndecan-1 levels in a mammalian (e.g., human) subject configured as a lateral flow assay (LFA) device. The assay device 10 is constructed with housing 12 containing a sample pad 14, a signal release pad 16 and at least one capture region 18, in this order. The sample pad 14, signal release pad 16 and capture region 18 are fluidly connected to provide a flowpath for the sample and an analyte contained therein to move from the sample pad 14 to the capture region 16. Generally, an absorption pad 26 may also be provided to draw the fluid through the assay device 10 by capillary action and absorb any excess fluid. The direction of the flowpath is indicated by "F" in FIG. 2.

The sample pad 14 is positioned at a first end of the housing 12 and is accessible from the housing 12 so as to allow the sample pad 14 to receive a sample, such as a drop of blood. A sample received by the sample pad 14 is typically conducted by capillary action into the housing 12 and along the flowpath.

The signal release pad 16 contains a signal member with binding specificity for syndecan-1 impregnated therein. The signal member is freely diffusible and able to be carried by fluid flow from the signal release pad 16 to the capture region 18. The signal member preferably produces an optically detectable analyte signal when the signal member is captured in the capture region 18 in an amount exceeding a minimum threshold.

The minimum threshold for producing the analyte signal may be selected by those skilled in the art to correlate with a concentration of syndecan-1 in the blood sample indicative of internal hemorrhaging or hemorrhagic shock. In this way, an analyte signal value less than the minimum threshold may indicate that the subject is not internally hemorrhaging or in hemorrhagic shock, and an analyte signal value above the minimum threshold may indicate the subject is internally hemorrhaging or in hemorrhagic shock. In preferred examples, the minimum threshold correlates to a concentration of syndecan-1 in the blood sample of at least 27 ng/ml. However, the minimum threshold may correlate to a concentration of syndecan-1 in the blood sample of at least 28 ng/ml, at least 29 ng/ml, at least 30 ng/ml, at least 50 ng/ml, at least 100 ng/ml, at least 150 ng/ml, at least 200 ng/ml, at least 300 ng/ml, at least 350 ng/ml, at least 400 ng/ml, or at least 450 ng/ml.

The signal member may be any suitable material that produces a signal that is optically detectable. Examples of an optically detectable signal may be a colorimetric change or fluorescence. An optically detectable signal may be observable by the naked eye or by using a device.

In some examples, the signal member may comprise a conjugated nanoparticle having an anti-syndecan-1 antibody immobilized thereon. Nanoparticles may be made of gold, gold-coated silicon, latex, or other suitable materials. Gold nanoparticles are preferred. The size of the particles and particle size distribution is preferably selected to allow the particles to be carried by fluid flow from the signal release pad 16 to the capture region 18. A suitable particle size may be 50 to 120 nm.

The capture region 18 is fluidly connected to the signal release pad 16 and has binding specificity for syndecan-1. Binding specificity for syndecan-1 may be provided by immobilizing anti-syndecan-1 antibodies to a substrate 24 in the capture region 18. The substrate 24 may be any suitable material, such as a porous membrane, nitrocellulose membrane, and the like.

Anti-syndecan-1 antibodies provided as part of the signal member (primary antibodies) and in the capture region 18 (secondary antibodies) are typically selected for binding different regions of the syndecan-1 protein so that both antibodies may bind simultaneously. Anti-syndecan-1 antibodies may be those commercially available or may be prepared by methods known in the art. Suitable commercially available antibodies include the Anti-SDC1 polyclonal antibody manufactured by Atlas Antibodies (HPA006185) which binds to the sequence identified in SEG ID NO:5.

The assay device 10 may also include a control region 20, preferably positioned after the capture region 18 in terms of the flow path. The control region 20 has binding specificity for syndecan-1 antibodies and produces an optically detectable control signal when the syndecan-1 antibodies are captured by the control region 20. In this way, the control region 20 enables a user to verify that the sample fluid has successfully flowed through the assay device and verify a negative reading.

Binding specificity for syndecan-1-antibodies may be provided by immobilizing anti-antibodies specific for the selected syndecan-1 antibody of the signal member to the substrate 24 in the control region 20. An anti-antibody specific for the syndecan-1 antibodies is not limited so long as it has binding specificity for the selected syndecan-1 antibody. A suitable anti-antibody specific for the syndecan-1 antibodies may be, for example, an anti-species antibody, such as a goat anti-mouse antibody.

The assay device 10 may include more than one capture region 18 fluidly connected to the signal release pad. For example, multiple capture regions may be provided by immobilizing additional lines of reagent material along the flowpath in a ladder arrangement. Alternatively, the device may include multiple parallel flowpaths with one or more respective capture regions. Advantageously, each of the plurality of capture regions 18 may have different sensitivities for different concentrations of syndecan-1 in the blood sample. For example, the capture regions 18 may have different respective binding affinities for syndecan-1 or different concentrations of anti-syndecan-1 antibodies. The use of a plurality of capture regions 18 having different respective binding sensitivities for an analyte can be used to provide a quantitative determination of the amount of analyte in the sample. The design of a quantitative lateral flow assay is known in the art. See, e.g., U.S. Pat. No. 9,851,364, incorporated herein in its entirety by reference.

An assay device having plurality of capture regions 18 may include a first analyte threshold corresponding to a first concentration of syndecan-1 and a second (or further) analyte threshold corresponding to a second (or further) concentration of syndecan-1. Thus, for an analyte signal value of less than the second threshold, but greater than the first threshold, a concentration of syndecan-1 elevated relative to normal levels in the blood sample, for example, may be indicated. An analyte signal value of greater than the second threshold may be indicated as a further elevated concentration of syndecan-1 in the blood sample. According to an example, the assay device may comprise first and second analyte thresholds which correspond respectively to a minimum threshold concentration of syndecan-1 in the blood sample of at least 27 ng/ml and to at least 150 ng/ml. The result may indicate a concentration range of syndecan-1 in the blood sample of a patient to help the user to confirm the likelihood of internal hemorrhaging and assess its severity.

Preferably, the housing 12 is configured as a hand-held device. Hand-held construction is advantageous for transporting and using the device in the field, such as a battlefield. The housing 12 may also be provided with a window 22 positioned over the capture region 18 to allow a user to visually inspect the capture region 18.

LFA devices are generally known in the art. See, e.g., U.S. Pat. No. 7,144,742, incorporated herein in its entirety by reference. Materials constituting the flow path F may be selected by those skilled in art. For example, the flowpath may be provided by one or more substrates that are able to convey a liquid from a first position to a second position and may be for example a capillary channel, a microfluidic pathway, or a porous carrier such as a lateral flow porous carrier. A porous carrier may comprise one or a plurality of porous carrier materials which may overlap in a linear or stacked arrangement or which are fluidically connected. The porous carrier materials may be the same or different. For example, untreated paper, cellulose blends, nitrocellulose, polyester, an acrylonitrile copolymer, rayon, glass fiber, and the like may also be employed as support matrix materials to provide flow. Suitably, the material of the signal release pad may be either glass fiber or cellulose filter. Buffers may also be used as known in the art. A suitable buffer may be 5 mM Borate, 10% sucrose, and 5% trehalose.

Methods of using the assay device 10 will now be described. A subject may be evaluated for trauma and, if the subject is suspected of suffering from internal hemorrhaging, a user (e.g., field medic) will perform an internal hemorrhage assay. Generally, the user will obtain a blood sample from a mammalian subject suspected of internal hemorrhaging, such as by finger prick. The blood sample may be applied to the sample pad 14 on a sample receiving portion 26 of the assay device 10. Capillary flow may pull the sample liquid through substrate 24 into the signal release pad 16 containing signal members which, in this example, are anti-syndecan-1 conjugated gold nanoparticles (GNPs). If syndecan-1 is present in the blood sample, it will bind to signal members and form a syndecan-GNP complex. The syndecan-GNP complex will be pulled further through the assay device 10 into substrate 24 and onto the capture region 18 containing immobilized anti-syndecan-1 antibodies. The GNP-syndecan-1 complex will bind to these immobilized antibodies, thereby immobilizing the complex in the capture region 18. This action will result in a "sandwich ELISA" in which the target sydecan-1 protein is caught between two antibodies (the primary and the secondary). The sample liquid flows further to the control region 20, which binds to any syndecan-GNP complex not immobilized in the capture region or non-complexed GNPs. Any remaining liquid will continue along the flow path until it reaches the absorption pad 26 at the end of the assay device, which will absorb the liquid.

Binding of the syndecan-GNP complexes in the capture region produces an optically detectable analyte signal value that may indicate if syndecan-1 is present and in an amount exceeding the minimum threshold, thereby indicating whether the patient is internally hemorrhaging. A positive test result may have two clearly visible lines corresponding to the capture region and control region. A negative test result may have only one clearly visible line (the control line).

In this example, if the analyte signal value is greater than or equal to a minimum threshold correlated to a concentration of the syndecan-1 in the blood sample of at least 27 ng/ml, the subject may be considered to be experiencing internally hemorrhaging. If the assay is positive, the patient may be immediately evacuated to a nearest field hospital or immediately be signaled for medevac. Additionally, the subject may be immediately administered a blood product transfusion, such as plasma. As the assay device may provide a result within 5 minutes, treatment may begin immediately. For example, immediate treatment may generally occur in the field prior to transporting the subject to a hospital setting.

The invention claimed is:

1. A method for determining a quantitative estimate of syndecan-1 levels in a mammalian subject suspected of internal hemorrhaging, the method comprising:
 a) applying a blood sample from the subject to a hand-held assay device capable of providing optical quantitation of the amount of syndecan-1 in the sample;
 b) measuring, by means of said assay device, an analyte signal value correlated to a concentration of the syndecan-1 in the blood sample;
 c) comparing the analyte signal value to a minimum threshold, wherein an analyte signal value less than the minimum threshold indicates that the subject is not internally hemorrhaging, and an analyte signal value above the minimum threshold indicates the subject is internally hemorrhaging,
 wherein the assay device comprises:
  a sample pad for receiving the blood sample,
  a signal release pad fluidly connected to the sample pad and containing a signal member with binding specificity for syndecan-1 and configured to produce an optically detectable analyte signal when an amount of the signal member captured by the capture region correlates to a concentration of the syndecan-1 in the blood sample exceeding the minimum threshold, and
  a capture region that is fluidly connected to the signal release pad and in which a capture reagent having binding specificity for syndecan-1 is immobilized.

2. The method according to claim 1, wherein the minimum threshold correlates to a concentration of the syndecan-1 in the blood sample of more than 27 ng/ml.

3. The method according to claim 1, wherein the minimum threshold correlates to a concentration of the syndecan-1 in the blood sample of more than 150 ng/ml.

4. The method according to claim 1, wherein a time between the applying step and the comparing step is 5 minutes or less.

5. The method according to claim 1, further comprising comparing the analyte signal value to a second minimum threshold.

6. The method according to claim 1, further comprising verifying a determination of the quantitative estimate of syndecan-1 levels in the mammalian subject by comparing the analyte signal value to a control signal.

7. A method of treating a mammalian subject suspected of internal hemorrhaging comprising:
 a) applying a blood sample from the subject to a hand-held assay device capable of providing optical quantitation of the amount of syndecan-1 in the sample;
 b) measuring, by means of said assay or assay device, an analyte signal value correlated to a concentration of the syndecan-1 in the blood sample;
 c) determining that the analyte signal value exceeds a minimum threshold correlated to a concentration of the syndecan-1 in the blood sample, wherein an analyte signal value less than the minimum threshold indicates that the subject is not internally hemorrhaging, and an analyte signal value above the minimum threshold indicates the subject is internally hemorrhaging; and
 d) administering a blood product transfusion to the subject,
 wherein the assay device comprises:
  a sample pad for receiving the blood sample,
  a signal release pad fluidly connected to the sample pad and containing a signal member with binding specificity for syndecan-1 and configured to produce an optically detectable analyte signal when an amount of the signal member captured by the capture region correlates to a concentration of the syndecan-1 in the blood sample exceeding the minimum threshold, and
  a capture region that is fluidly connected to the signal release pad and in which a capture reagent having binding specificity for syndecan-1 is immobilized.

8. The method of treating a mammalian subject according to claim 7, wherein the minimum threshold is correlated to a concentration of the syndecan-1 in the blood sample of at least 27 ng/ml.

9. The method of treating a mammalian subject according to claim 7, wherein the minimum threshold is correlated to a concentration of the syndecan-1 in the blood sample of at least 150 ng/ml.

10. The method of treating a mammalian subject according to claim 7, wherein the blood product is plasma.

* * * * *